US006840905B2

United States Patent
Gotschim et al.

(10) Patent No.: US 6,840,905 B2
(45) Date of Patent: *Jan. 11, 2005

(54) SYSTEM AND METHOD OF AUTOMATING MULTIDIMENSIONAL SCALING FOR PSYCHOPHYSICS

(75) Inventors: Christian Peter Gotschim, St. Poelten (AT); Yue Qiao, Longmont, CO (US); Jeff Wang, Longmont, CO (US)

(73) Assignee: International Business Machines Corporation, Armonk, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/394,301

(22) Filed: Mar. 20, 2003

(65) Prior Publication Data

US 2003/0195395 A1 Oct. 16, 2003

Related U.S. Application Data

(62) Division of application No. 09/876,501, filed on Jun. 6, 2001, now Pat. No. 6,569,096.

(51) Int. Cl.[7] .................................................. A61B 5/00
(52) U.S. Cl. ........................................................ 600/300
(58) Field of Search ................................. 600/300–301, 600/558, 587; 434/235, 262; 128/920

(56) References Cited

U.S. PATENT DOCUMENTS

| 5,255,243 A | 10/1993 | Kitazawa |
| 5,295,243 A | 3/1994 | Robertson et al. |
| 5,596,703 A | 1/1997 | Eick et al. |
| 5,664,158 A | 9/1997 | Larimer |
| 5,692,502 A | 12/1997 | Alpert |
| 5,748,783 A | 5/1998 | Rhoads |
| 5,986,673 A | 11/1999 | Martz |
| 6,190,314 B1 * | 2/2001 | Ark et al. ................. 600/300 |
| 6,261,299 B1 * | 7/2001 | Chakeres ................. 600/300 |
| 6,569,096 B2 * | 5/2003 | Gotschim et al. ......... 600/300 |

* cited by examiner

*Primary Examiner*—Michael C Astorino
(74) *Attorney, Agent, or Firm*—David W. Victor; Konrad Raynes & Victor LLP

(57) ABSTRACT

Disclosed is method, system, and program for defining and administering a test to determine human perceptions of observable samples, such as printed text or images, sounds, motion pictures, etc. based on multiple factors. A displayable test building window includes input fields to receive input on at least one observable sample set according the multidimensional scaling experiment. Generated in a data gathering window is at least one perception input field for each observable sample set. The observer is capable of entering perception information in each input field concerning the observable samples. Observer perception input on the observable samples is received and stored. Statistical analysis is then performed on the entered perception input. A report is generated displaying the results of the multidimensional scaling calculations in the form of plots.

8 Claims, 16 Drawing Sheets

SYSTEM AND METHOD OF AUTOMATING MULTIDIMENSIONAL SCALING FOR PSYCHOPHYSICS

CROSS-REFERENCE TO RELATED APPLICATION

This application is a Divisional application of and commonly-assigned, U.S. Pat. No. 6,569,096, application Ser. No. 09/876,501, titled "SYSTEM AND METHOD OF AUTOMATING MULTIDIMENSIONAL SCALING FOR PSYCHOPHYSICS," by C. P. Gotschim et al., filed on Jun. 6, 2001, and which is incorporated herein by reference in its entirety.

BACKGROUND OF THE INVENTION

1. Field of the Invention

The present invention relates to a system and method for automating the process of conducting psychophysics experiments. More specifically, a system and method for conducting the multidimensional scaling method for psychophysics.

2. Description of the Related Art

Psychophysics is commonly defined as the quantitative branch of the study of perception, examining the relations between observed stimuli and responses and the reasons for those relations. Since its inception, psychophysics has been based on the assumption that the human perceptual system is a measuring instrument yielding results (experiences, judgments, responses) that may be systematically analyzed.

Because of its long history, its experimental methods, data analyses, and models of underlying perceptual and cognitive processes have reached a high level of refinement. For this reason, many techniques originally developed in psychophysics have been used to unravel problems in learning, memory, attitude measurement, and social psychology.

In the general paradigm of visual psychophysics, a human subject is presented with accurately controlled stimuli, and in certain prescribed ways, is asked what he sees. From the results of these experiments, inferences can be made about the nature of visual processes.

In the printing industry, visual psychophysics testing can be used to determine correlations of human perceptions of print quality with physical measurements such as, for example, gray levels, halftone screening, density control, and the like. Psychophysics testing methods which have been used in the printing and other display industries include the Paired Comparison, Ranking Order, Rating Scales, Ratio Scales, Categorical Scales, Multidimensional Scaling methods. The above methods themselves and their statistical analysis are fully described in James Bartleson and Franc Grum, "Visual Measurements", which is Volume 5 in "Optical Radiation Measurements", Academic, Orlando, 1984; and J. P. Guilford, "Psychometric Methods," McGraw-Hill, $2^{nd}$ Edition, 1954, which publications are incorporated herein by reference in their entirety.

Multidimensional Scaling ("MDS") method involves identifying relative similarity and differences between a group of three samples. The observer is asked to determine which two samples have the most differences and which two samples have the least differences. A determination of which factors make the most difference in sample quality can be determined from the MDS method.

The process of conducting a psychophysics experiment is time and labor intensive. It involves the generation of the samples to be observed, the randomization of the samples, the observation of the samples by the test subjects, the collection of the observation data, and the statistical analysis of the data. Many experiments require 15 to 20 or more observers to view the samples. Thus an experimenter's job would involve generating the samples, randomizing the samples for each of the 15–20 observers, collecting the data during each of the 15–20 observation sessions, and conducting the statistical data analysis by hand.

Because of the time and labor intensive nature of this testing, there is a need to automate the process, thereby greatly reducing the testing time.

SUMMARY OF THE PREFERRED EMBODIMENTS

To overcome the limitations in the prior art described above, preferred embodiments disclose a method, system, and program for comparing multiple factors using multidimensional scaling analysis. Sample sets are generated where each sample in the sample set is created by a different algorithm made up of at least three factors. Relative differences between the samples in the sample set is observed and recorded. Statistical analysis is then performed on the observed differences between the samples in the sample set, and the results of the analysis are displayed as plots.

In preferred embodiments, a displayable test building window, which includes input fields to receive input on at least one observable sample set, is used to set up the observation and recording process. A data gathering window is generated containing at least one perception input field for each observable sample set. The observer is capable of entering perception information in each input field concerning the observable samples. Observer perception input on the observable samples is received and stored.

Preferred embodiments provide an improved method and apparatus for testing definition and generation for multidimensional scaling using a GUI program for graphically specifying data items and computations to be performed on the data. The present invention provides a psychophysics testing tool that uses objects to define both testing layout and the data aspects of the testing. Unlike the prior art, the present invention provides a graphical way to accomplish both of these testing aspects. That is, a GUI program is used to facilitate all testing steps, including sample generation, randomization, observation, data collection, and analysis.

DETAILED DESCRIPTION OF THE PREFERRED EMBODIMENTS

The system and method of the described implementations allows testers to collect and analyze data concerning the ability of humans (i.e. observers) to detect, recognize, discriminate or assign qualitative labels to either single objects or a group of objects. In certain implementations, a graphical user interface (GUI) program is used for test building, test taking, and data analysis for variety of psychophysics methods. Co-pending, commonly assigned U.S. patent application Ser. No. 09/354,535, entitled "Method and System for Gathering and Analyzing Psychophysics Data" discloses the test building, test taking process, and the GUI interface used for six different types of psychophysics experiments, and is incorporated herein by reference in its entirety. In preferred embodiments, the Multidimensional Scaling method ("MDS method") is built along side the other psychophysics tests disclosed in application Ser. No. 09/354,535 and can be used in conjunction with the other methods in a single test package.

In the following description, reference is made to the accompanying drawings which form a part hereof, and which illustrate several embodiments of the present invention. It is understood that other embodiments may be utilized and structural and operational changes may be made without departing from the scope of the present invention.

Figure 1:
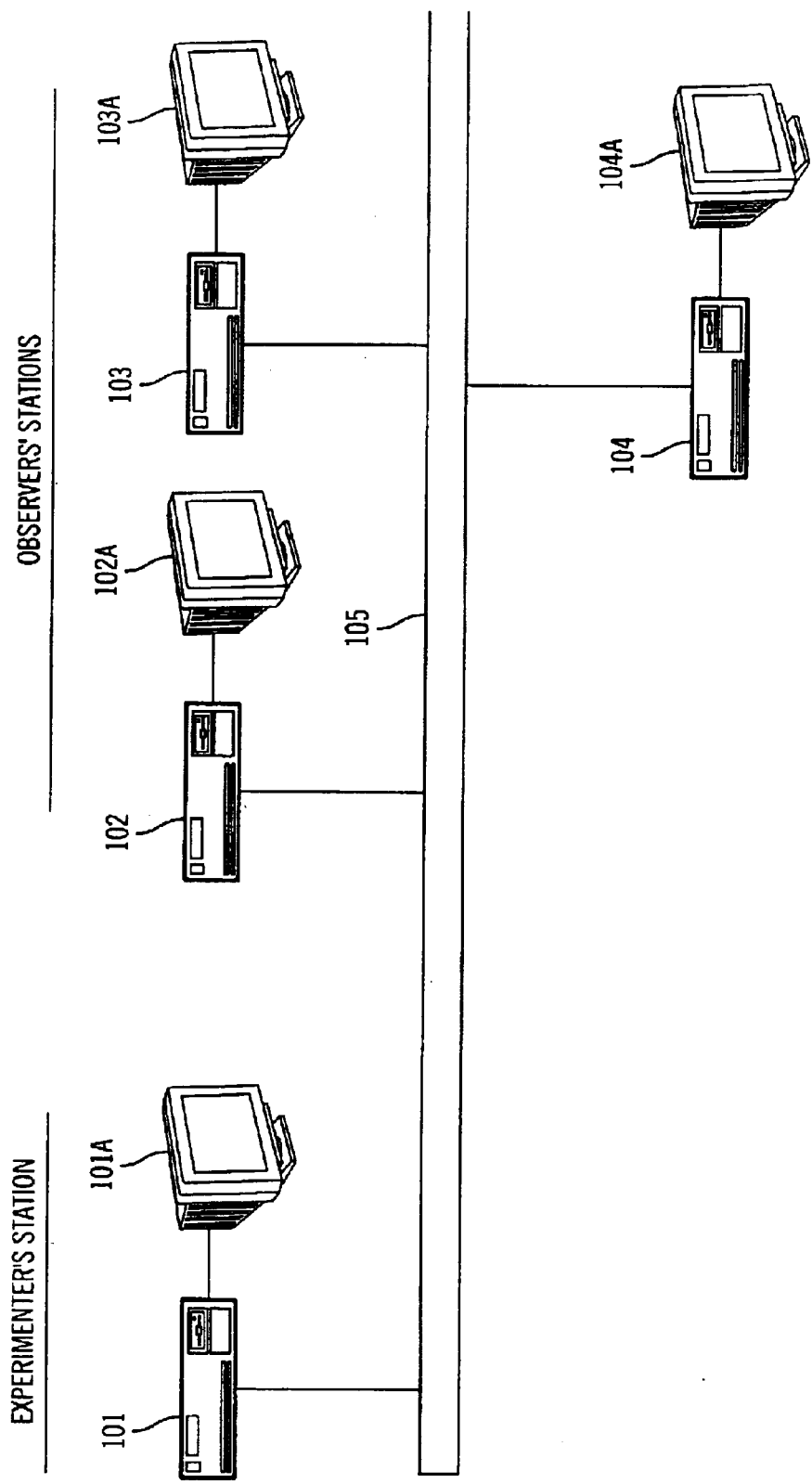
FIG. 1 is a block diagram illustrating a computing environment in which preferred embodiments of the present invention are implemented.

FIG. 1 illustrates a computing environment in which preferred embodiments are implemented. The preferred embodiment psychophysics testing system is implemented in a computer program that runs in a plurality of computers 101, 102, 103, and 104. These computers 101–104 may be any computer device known in the art, such as a desktop computer, laptop computer, workstation, mainframe, server, personal digital assistant (PDA), etc. The computers 101–104 would include an operating system 8 such as AIX, OS/390, UNIX, OS/2, MVS, WINDOWS NT, 95/98, LINUX, etc. A network system 105 links computers 101–104. Network 105 may be comprised of any suitable network architecture known in the art, such as LAN, Ethernet, WAN, Token Ring, LocalTalk, the Internet, etc. Alternatively, there may be separate and different networks between computers 101–104.

Computers 101–104 may include attached display monitors 101A–104A, which may be any suitable device known in the art. An input device (not shown) would also be provided with computers 101–104 to allow the examiners and observers to enter data into computers 101–104. This input device may be comprised of any input means known in the art, including a mouse, keyboard, touch screen display, voice activated input, electronic pen, etc.

In this embodiment, computers 101–104 are divided into an experimenter's station and the observers' stations. The experimenter uses computer 101 to set up and administer the testing. Computers 102–104 are used by the observers in taking the test. It can be appreciated that the testing system need not consist of a plurality of computers. In an alternative embodiment, a single computer could be employed wherein the experimenter would first set up the test and then allow the observer to take the test at the same computer. The test may be designed such that only one observer takes the test at a time. In this way, each observer will view the same print samples, thereby avoiding any variance in the test subject matter presented to the observers. In such case, only one observer computer needs to be available for testing.

Preferred embodiments provide a psychophysics testing tool that uses objects to define both testing layout and the data aspects of the testing. The preferred embodiments provide a graphical user interface (GUD to accomplish all testing steps, including sample generation, randomization, observation, data collection, and analysis. The preferred psychophysics tool is comprised of three program components: a Test Set-Up Program for sample generation and randomization; a Test Administration Program for sample observation and data collection; and a Data Analysis Program for statistical calculations and analysis of the data as well as the display of the test results.

The logic of the Test Set-Up Program and Test Administration Program is very similar to the logic disclosed in U.S. patent application Ser. No. 09/354,535. For example, as in U.S. patent application Ser. No. 09/354,535, the Test Set-Up Program portion of the GUI will record the name or title of the test, the number of tests to be performed, and the particular type of psychophysics tests to be performed, which in this case the experimenter will select "Multidimensional Scaling" as the test method. Similarly, the Test Administration Program portion of the GUI will collect information on the test subject, record the test taker's psychophysical response to the test, and lead the test taker through each set of samples until the test in complete.

In the preferred embodiments for the multidimensional scaling method, the experimenter will perform comparative analysis between three samples to determine which two samples have the most differences and which two samples have the least differences, wherein each sample set contains three samples. Each sample is produced using a unique print algorithm with varying values of print factors such as half-tone screen, sharpening, smoothing, resolutions, etc. A hard copy of each print sample is made for use in the experiment. The key aspect of the multidimensional scaling experiment is to determine the correlation between the differing factors and print quality. The typical comparative test involves printing the same image on at least three different printers, such as IBM, HP, LEXMARK, CANON, XEROX, etc.** to create a sample set of the same image using the unique algorithm of each printer. The experimenter then runs a comparative analysis of the images from the varying printers during the multidimensional scaling test method. By using multiple sample sets of differing images, the experimenter can get more accurate data on which factors contribute most to differences in print quality since each printer uses a unique combination of factor values to print the image.

**IBM is a registered trademark of the International Business Machines Corporation; LEXMARK is a registered trademark of the Lexmark International, Inc., CANON is a registered trademark of the Canon Kabushiki Kaisha Corporation.

Operation of Interface

Figure 2:
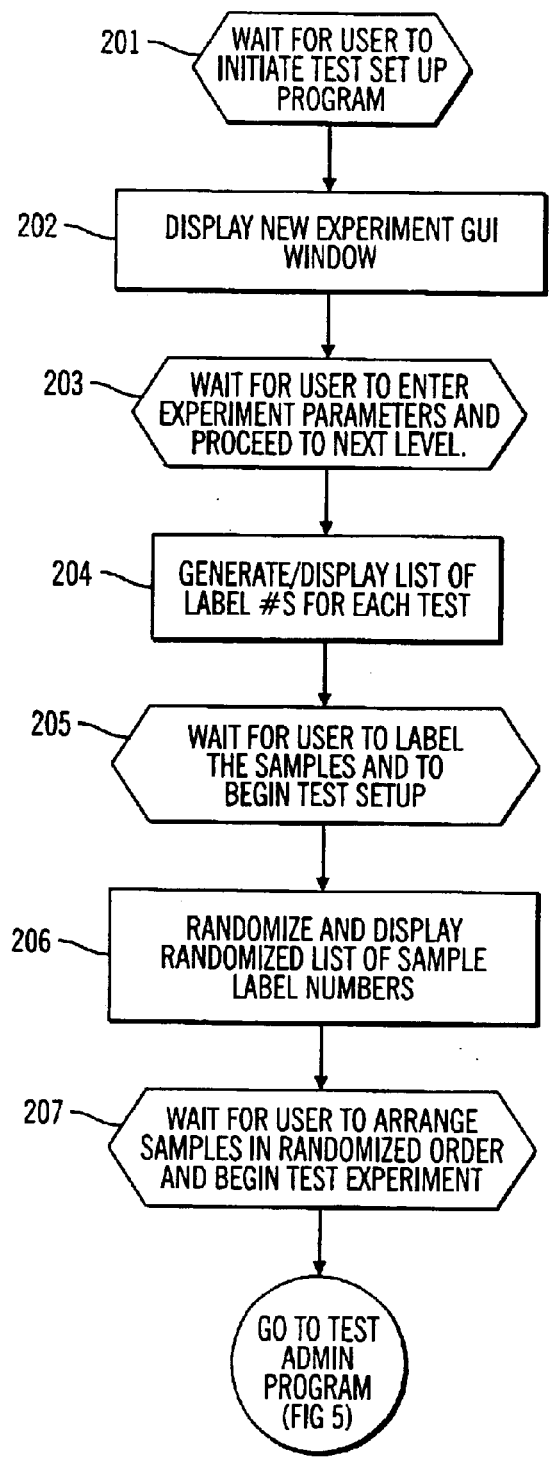
FIG. 2 illustrates logic to set up a psychophysics test for later test administration in accordance with preferred embodiments of the present invention.
Figure 3:
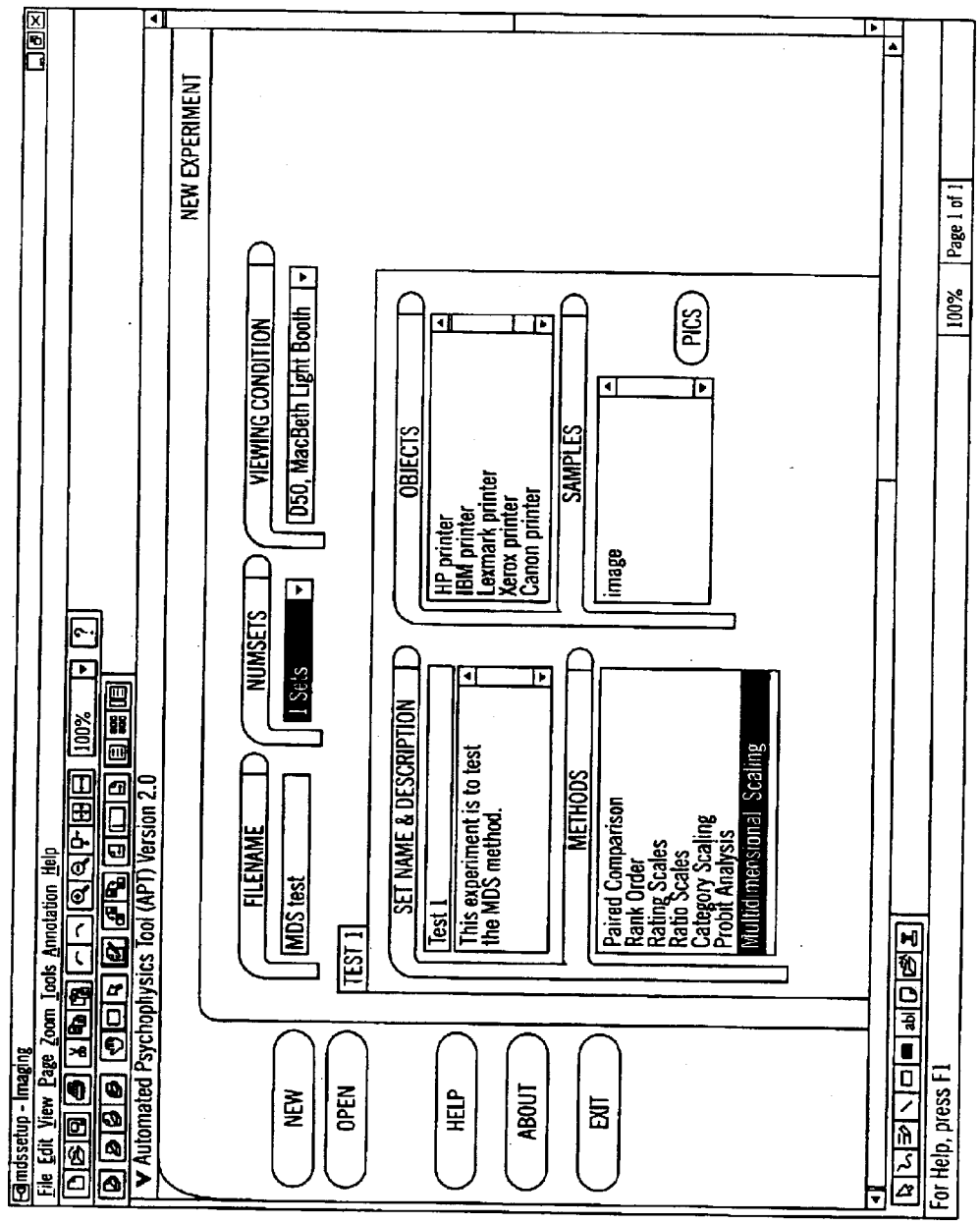
FIGS. 3 and 4 illustrate graphical user interface (GUI) panels displayed on a computer monitor to define a psychophysics experiment in accordance with preferred embodiments of the present invention.
Figure 4:
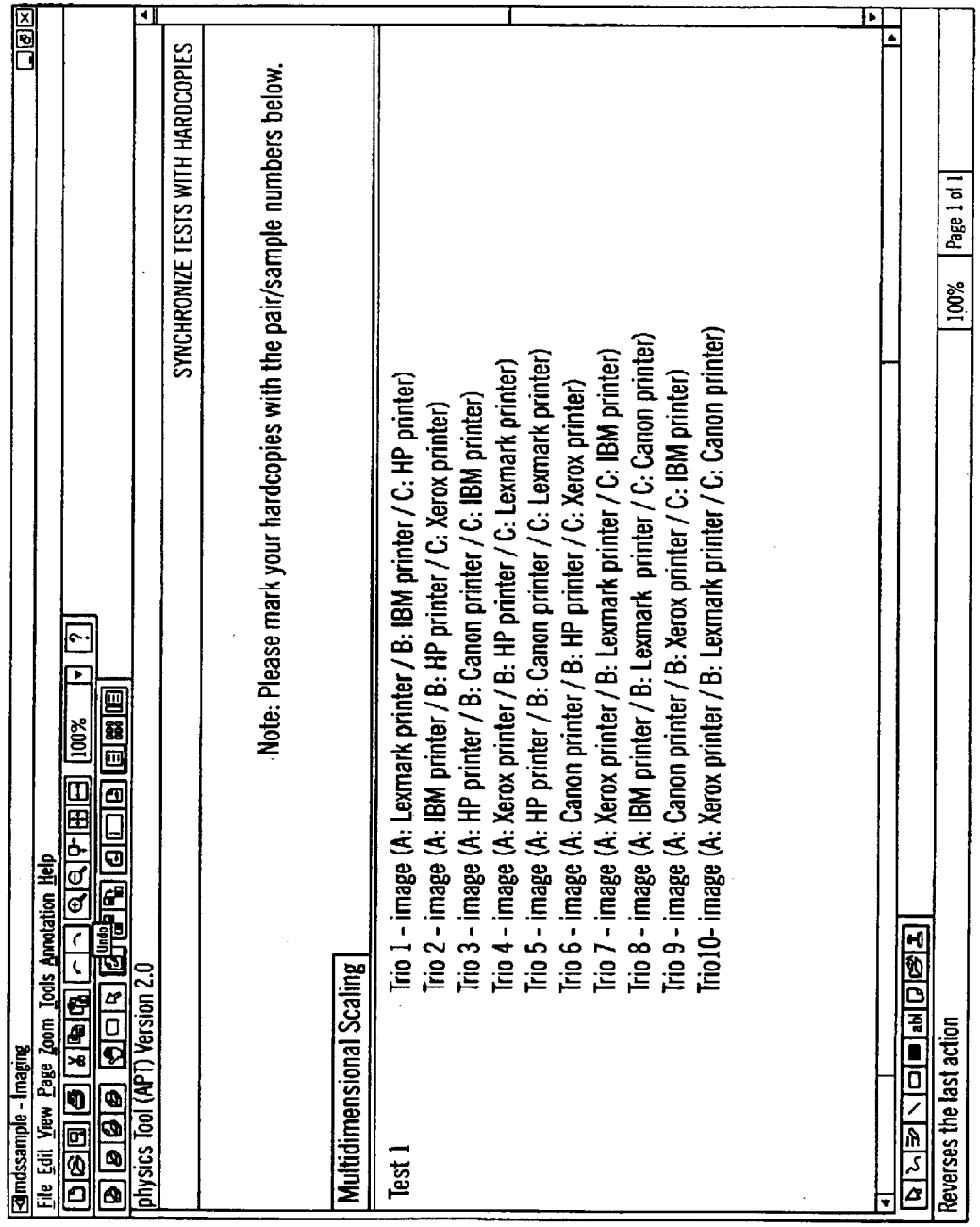
Figure 5:
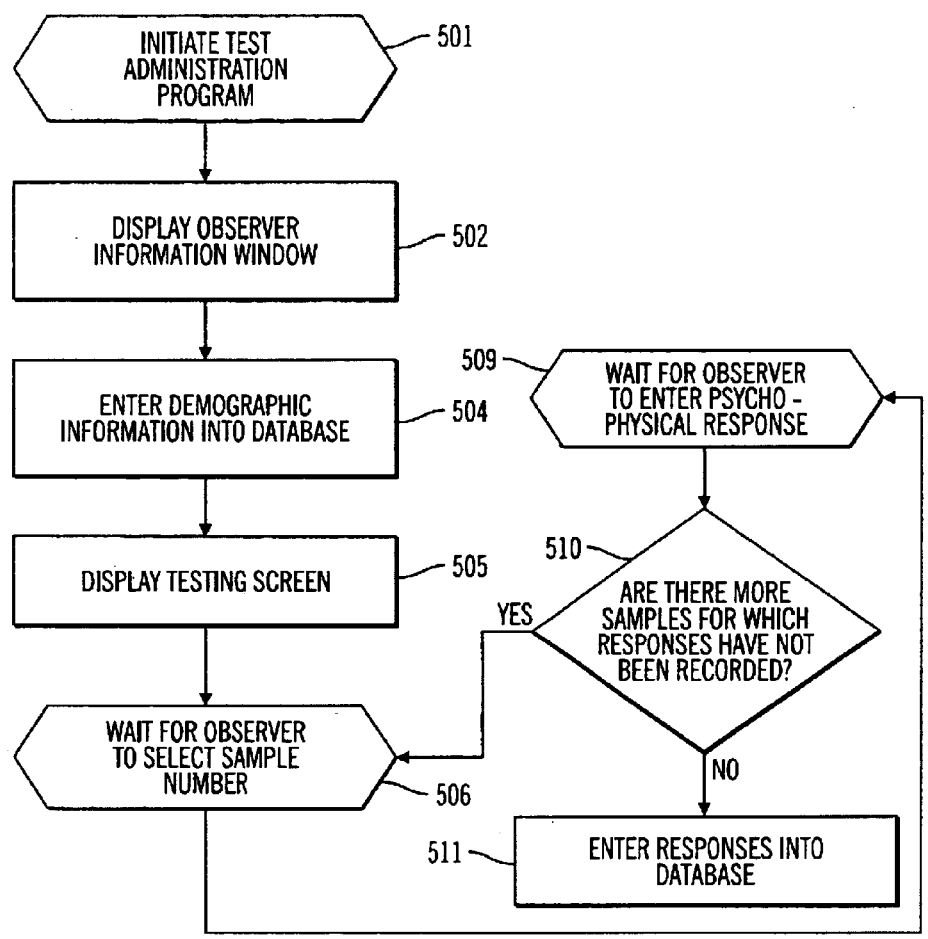
FIG. 5 illustrates logic to administer a psychophysics test in accordance with preferred embodiments of the present invention.
Figure 6:
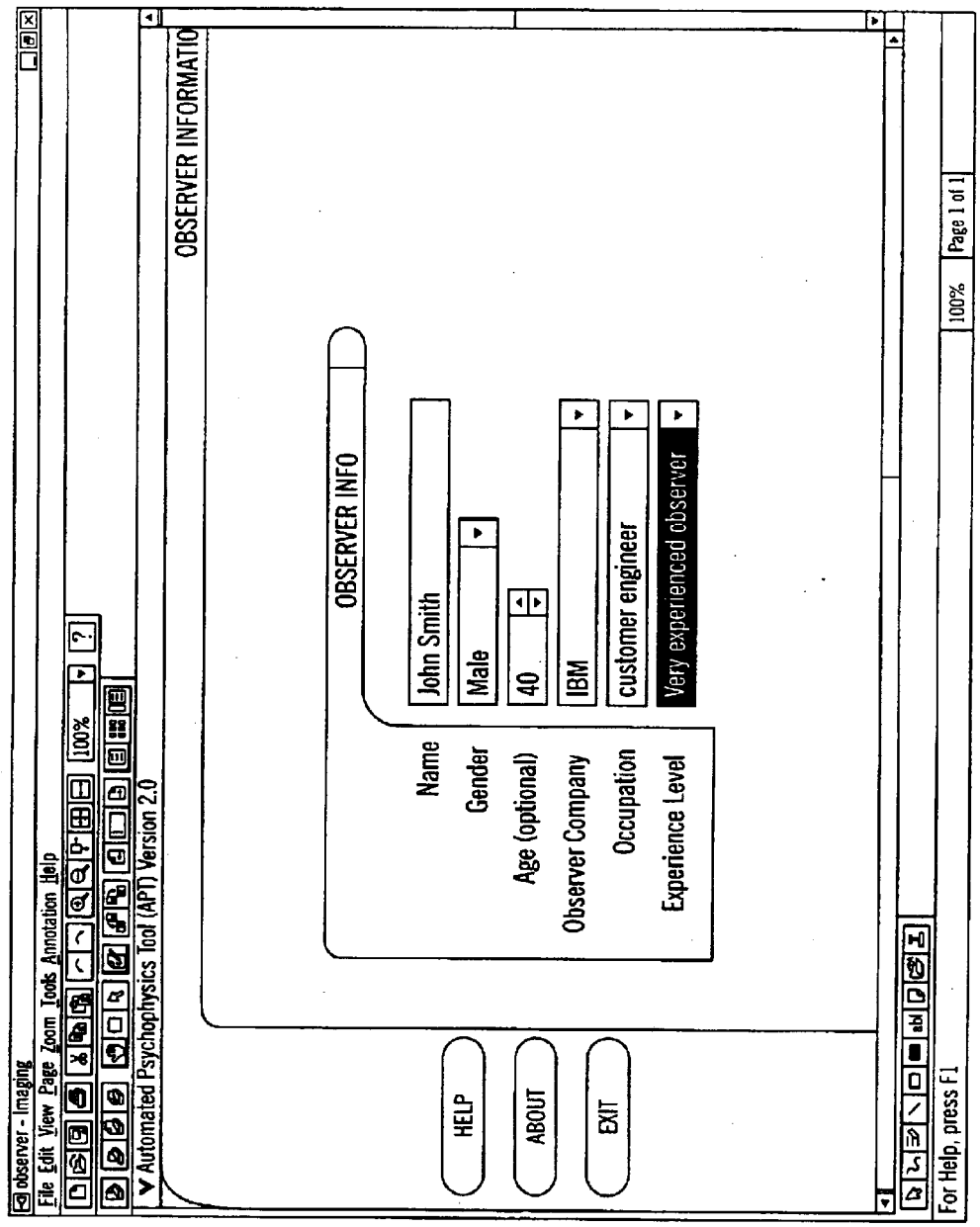
FIGS. 6 and 7 illustrate graphical user interface (GUI) panels displayed on a computer monitor to receive observer input during a psychophysics experiment in accordance with preferred embodiments of the present invention.
Figure 7:
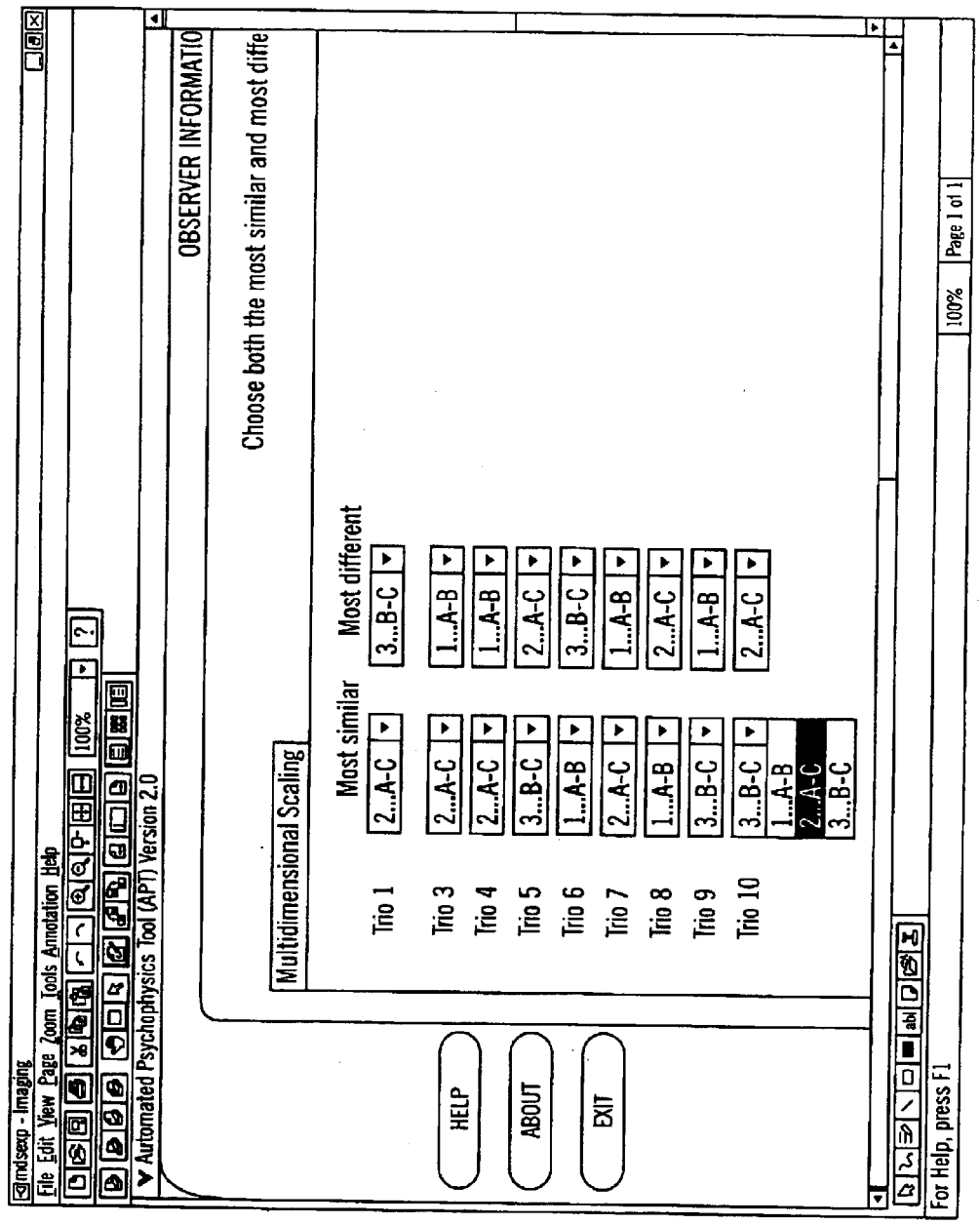
Figure 8:
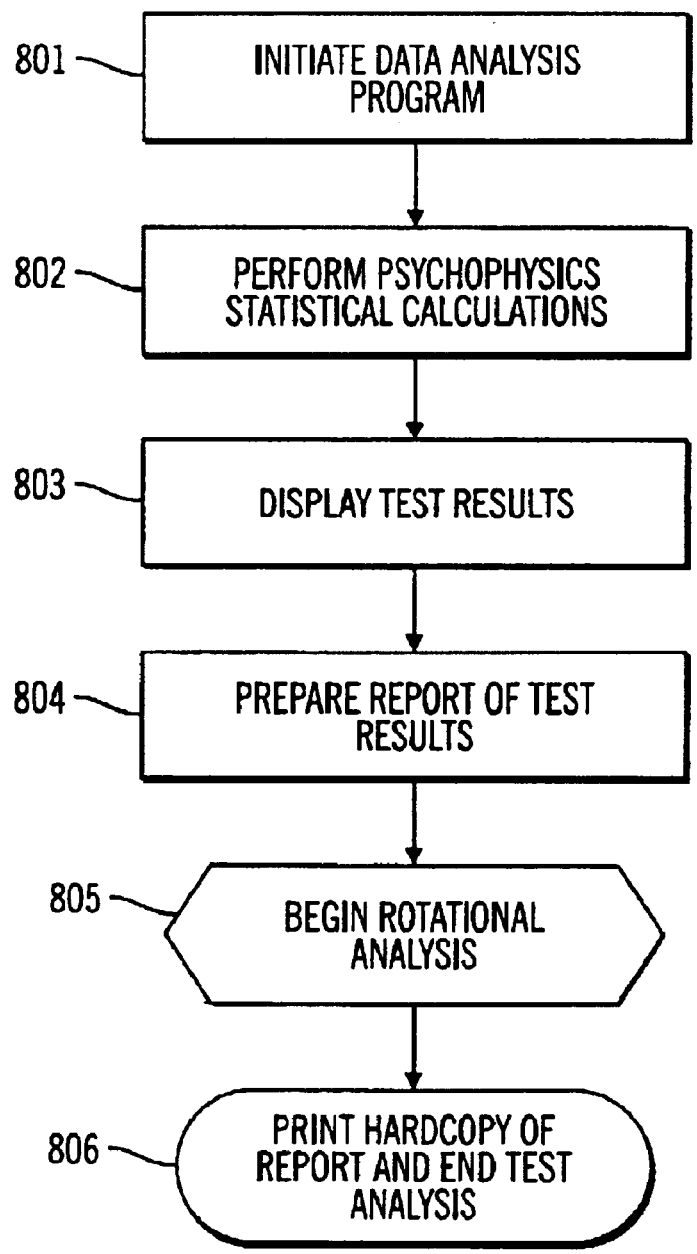
FIG. 8 illustrates logic to analyze the psychophysics test data in accordance with preferred embodiments of the present invention.

FIGS. 2, 5 and 8 illustrate the program logic implemented in computers 101–104 within an application program to conduct the psychophysics testing and analysis. The logic of FIGS. 2, 5, and 8 may generate GUI interfaces to sequence (1) the experimenter through a series of steps in setting up the testing parameters, (2) the observers in recording their observations, and (3) the experimenter in reviewing the testing results. FIGS. 3-4, 6-7, 9-16 illustrate examples of GUIs displayed on the display monitors 101A–104A, which guide the experimenter and the observers through the program.

FIG. 2 illustrates logic implemented in computers 101–104 within an application program to conduct the Test Set-Up Program. Referring to FIG. 2, control begins at block 201 which represents computer 101 waiting for an experimenter to invoke the psychophysics program application. Control transfers to block 202 where computer 101 displays a new experiment window as seen in FIG. 3, and then to block 203 where the computer waits for the experimenter to enter the experiment parameters. For the case of multidimensional scaling method, the preferred embodiment requires selecting the number of printers being compared (Listed as OBJECTS in FIG. 3) and the number and identity of the images which are to be observed (Listed as SAMPLES in FIG. 3). Additional parameters such as the name of the experiment, the particular method being tested (i.e. multidimensional scaling), etc. are also entered at this time.

By setting the number of printers and the number of images to be compared, the GUI, using a known algorithm, will calculate the number of samples to be displayed to the test taker/observer. The algorithm being:

number of samples sets per image=$(n)(n-1)(n-2)/6$, where $n$=number of printers.

For example, if only three printers are being compared, then the number of samples sets per image, $(3)(2)(1) \div 6$ equals 1, meaning that only one sample set will be required per image. Thus, depending on the number of images set by the experimenter, there will be a same number of sample sets. However, if four printers are being compared, then $(4)(3)(2) \div 6$ will mean that four sample sets for each image will be presented to the test taker. Thus for three images, the test taker/observer will have a chance to input his/her response for twelve sample sets. In alternative embodiments, sample sets can be generated using the same printer using different print algorithms (i.e. different combination of factors) to produce an image, wherein n=the number of different print algorithms. Thus, the correlation between the factors and the print quality can still be determined.

When the experimenter enters all the parameters, control transfers to block 204 where computer 101 generates and displays a list of all samples along with their label number assignments for the sample sets being presented to the test taker. FIG. 4 displays an example where five printers are being compared using one image. Thus, $(5)(4)(3) \div 6 = 10 \times 1$ image equals ten sample sets. On the other hand, if four printers and three images are used, twelve sample sets will be displayed to the experimenter. The experimenter can then verify that the correct sample sets will be tested. Control then transfers to block 205 where the computer waits for the experimenter to complete labeling the hard copy samples with the assigned label numbers, and begin the physical test setup.

For the physical test setup, control transfers to block 206 where the computer randomizes the order of the sample label numbers and displays the randomized order of the sample sets. Control then transfers to block 207 where the computer waits for the experimenter to arrange the samples in the randomized order displayed on computer monitor 101A and to begin the experiment.

FIG. 5 illustrates logic implemented in computers 101–104 within an application program to conduct the Test Administration Program. The program's control initiates at block 501. Control transfers to block 502 which causes the computer to display an observer information screen or screens, wherein in the preferred embodiment, the test taker is prompted to enter his/her name, sex, age, demographic information, etc. An example of the observer information input screen is seen in FIG. 6. Control then transfers to block 504 where the computer enters and stores the test taker data into the database portion of the program.

Control transfers to block 505 where the computer displays a test screen listing all the sample sets being tested (i.e. trio of samples) and a scroll menu to record the responses of the test taker. For multidimensional scaling, the test taker is asked which two of the three samples are most different, and which two of the three samples are least different. An example of the test screen is seen in FIG. 7. Control transfers to block 506 where the computer waits for the observer to select the first sample set in the randomized list of sample sets to be viewed. Control transfers to block 509 where the computer waits for the observer to record a selection which reflects the observer's psychophysical response to the sample. In alternative embodiments, the computer can be programmed to display an on-screen image corresponding to the hard copy sample set being observed as the observer selects (or hi-lights) the sample set. Thus, in a situation where more than one image is used, the on-screen image can serve as a cross check for the observer to verify that the labeled hard copy sample being viewed does indeed correspond with the sample set on the screen.

Block 510 represents a decision loop. If there are additional sample sets to be viewed by the test taker, control returns to block 506 where the test taker will select the next sample set on the test screen. However, if there are no additional samples to be viewed, then control transfers to block 511 where the computer stores all of the test taker's selections into the program's database or other data structure, thus concluding the Test Administration portion of the program. The test taker may then take additional tests using other psychophysics methods such as Paired Comparison, Ranking Order, Rating Scales, Ratio Scales, Categorical Scales or end the testing at that time. In preferred embodiments, the test taker must enter all responses for all possible tests before the program will proceed to the next stage of the Data Analysis Program.

Figure 9:
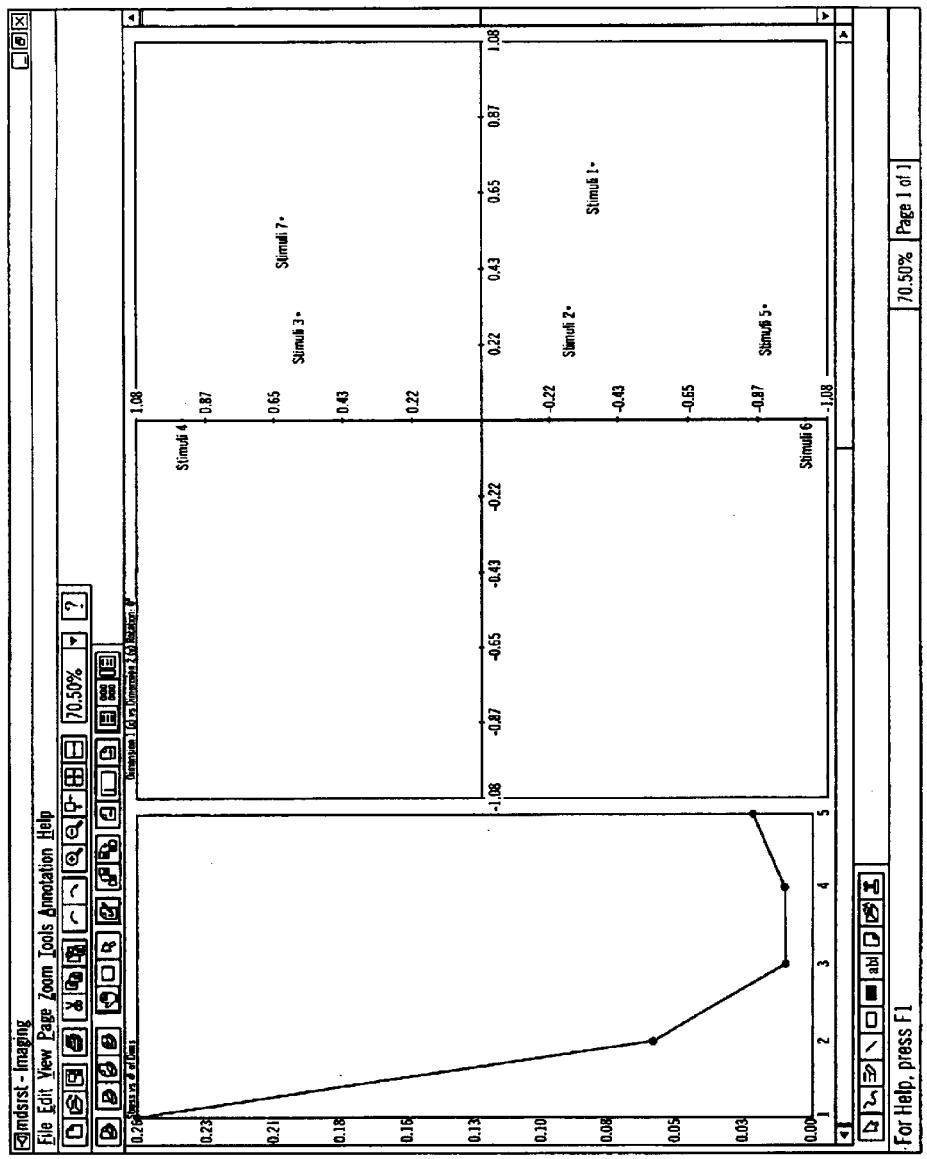
FIGS. 9-12 illustrate graphical user interface (GUI) panels displayed on a computer monitor including statistical analysis of the psychophysics data entered by the observer.

FIG. 8 illustrates logic implemented in computers 101–104 within an application program to conduct the Data Analysis Program portion of the program. The program's control initiates at block 801. Control transfers to block 802 which causes the computer to perform the psychophysics statistical calculations using the previously stored data. For multidimensional scaling method, either the classical MDS (Metric MDS) or modern MDS (Non-Metric MDS) statistical calculation is used. Both statistical calculations are well-defined in the prior art. Commercial software for statistical calculations currently exists which will do the MDS calculations and present the test results as text data in a table. However, current MDS software is not designed for psychophysics and cannot be used for psychophysics without tedious conversion by hand from the format presented by the existing software. Moreover, the text data is difficult to interpret, and makes very little sense to one of ordinary skill in the psychophysics field. Therefore, in the preferred embodiments, the test results are displayed in a plot format for a more intuitive interpretation of the data at block 803, where the computer displays the test results plot along with the text data on an information screen. In alternative embodiments, only the test results plot can be used, since the plot will make more intuitive sense in psychophysics. An example of the test result page is seen in FIG. 9, with a closeup of the test result page shown in FIG. 10.

Figure 10:
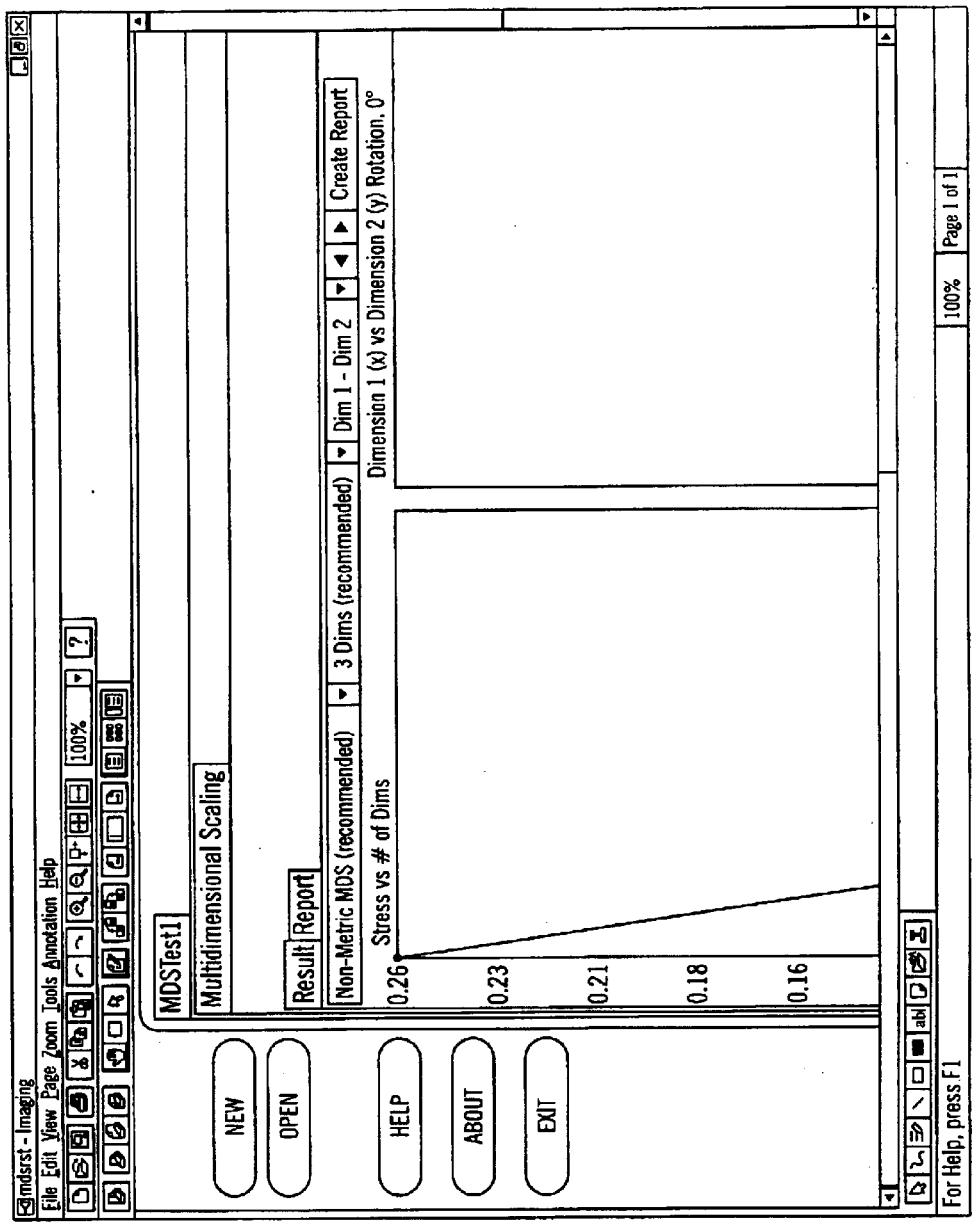
Figure 11:
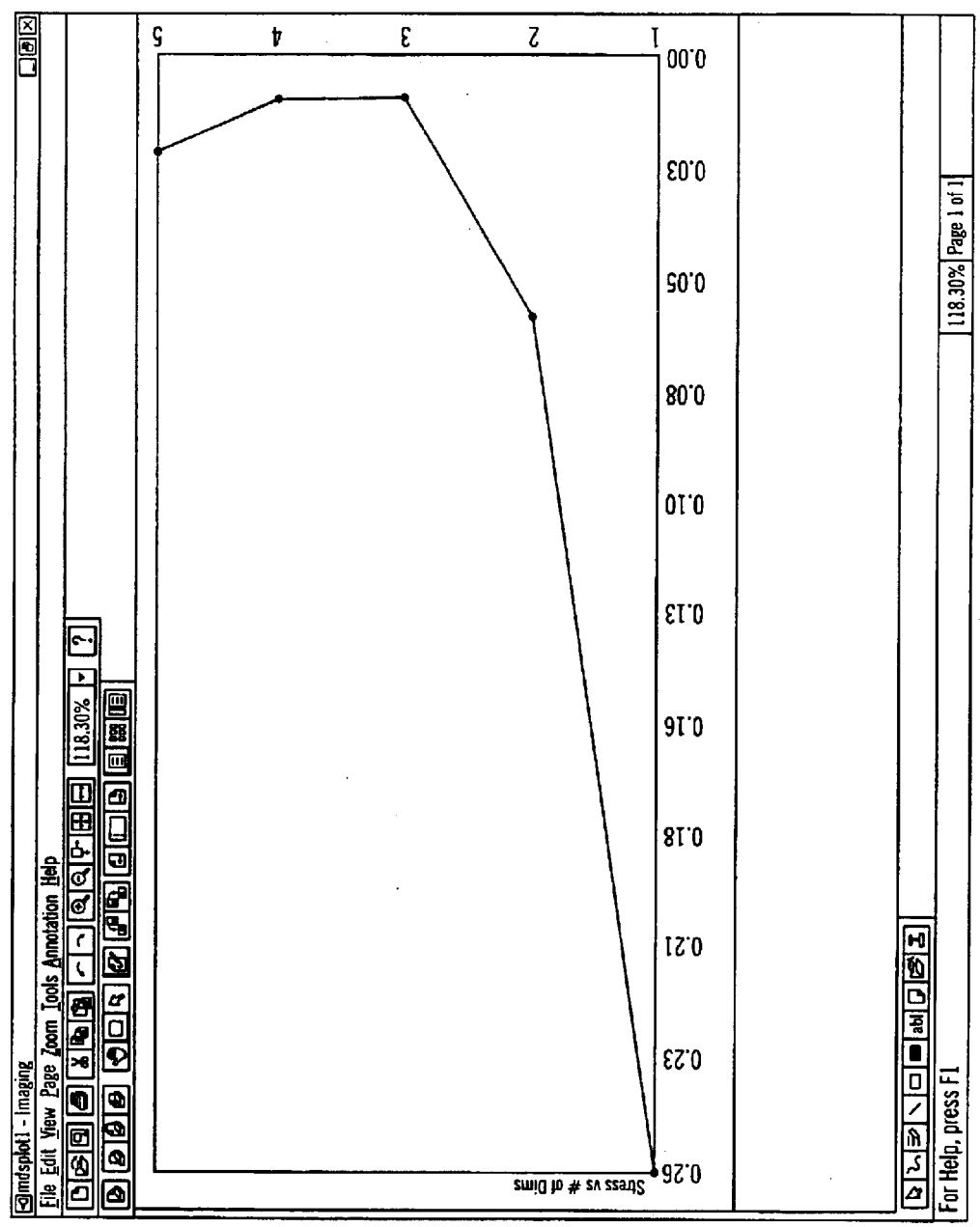
Figure 12:
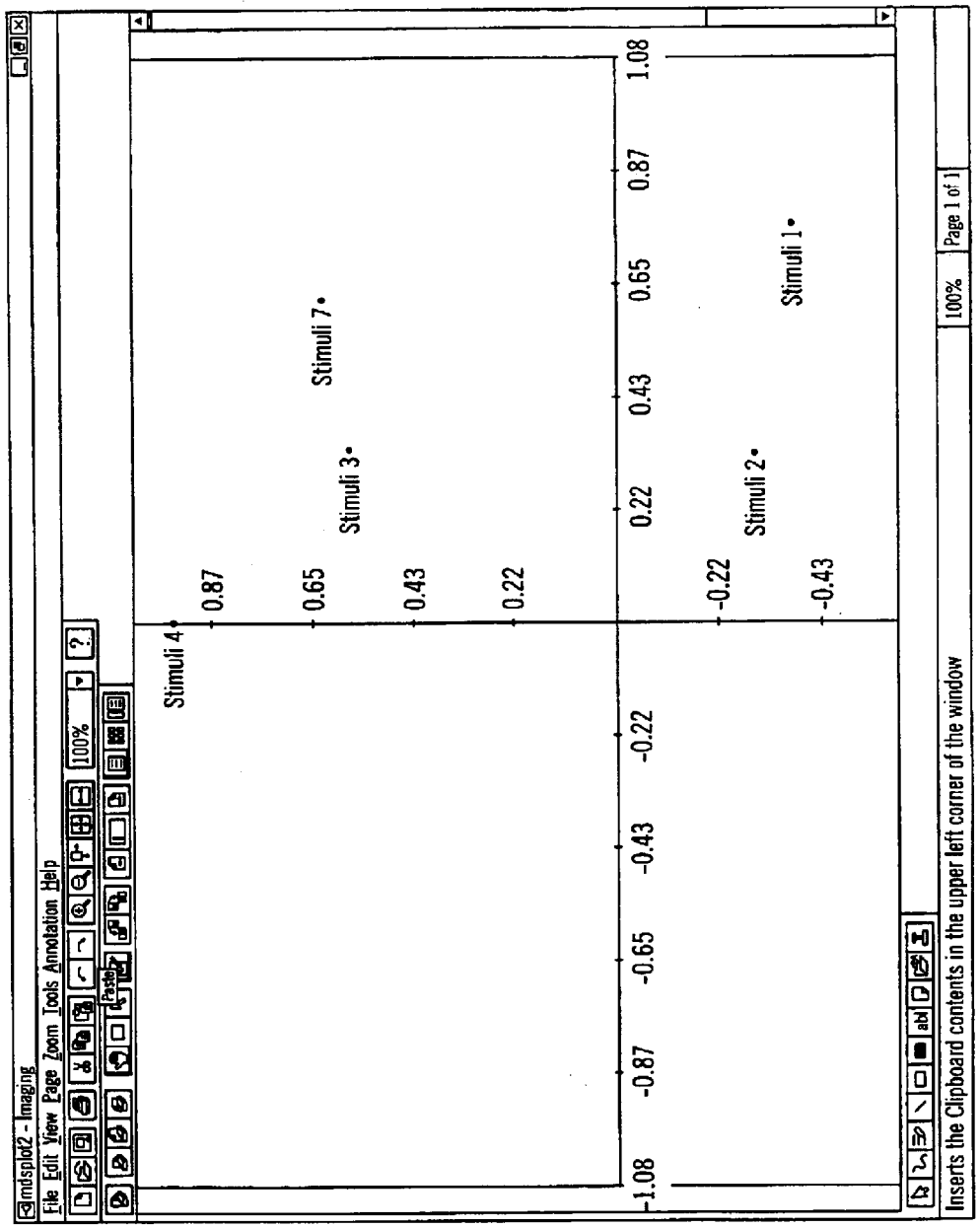
Figure 13:
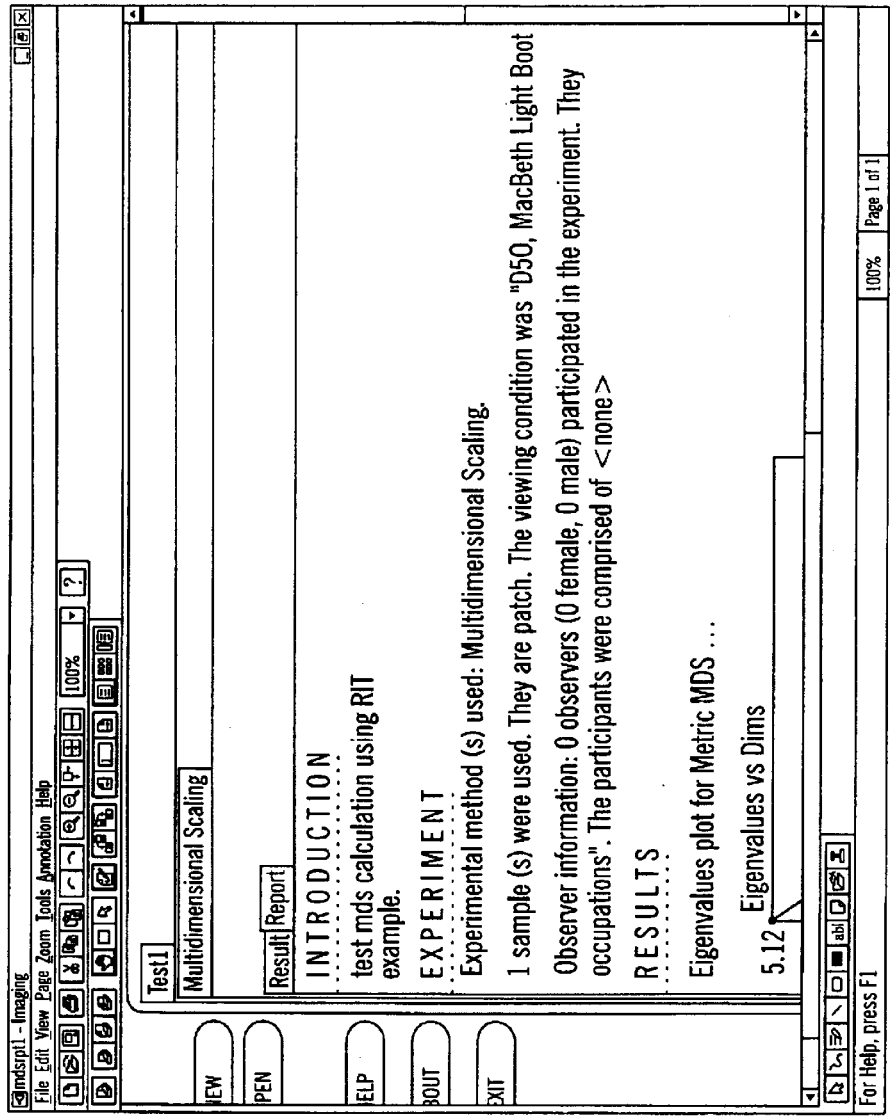
FIGS. 13-16 illustrate graphical user interface (GUI) panels displayed on a computer monitor presenting an automated report in accordance with the preferred embodiments of the present invention.
Figure 14:
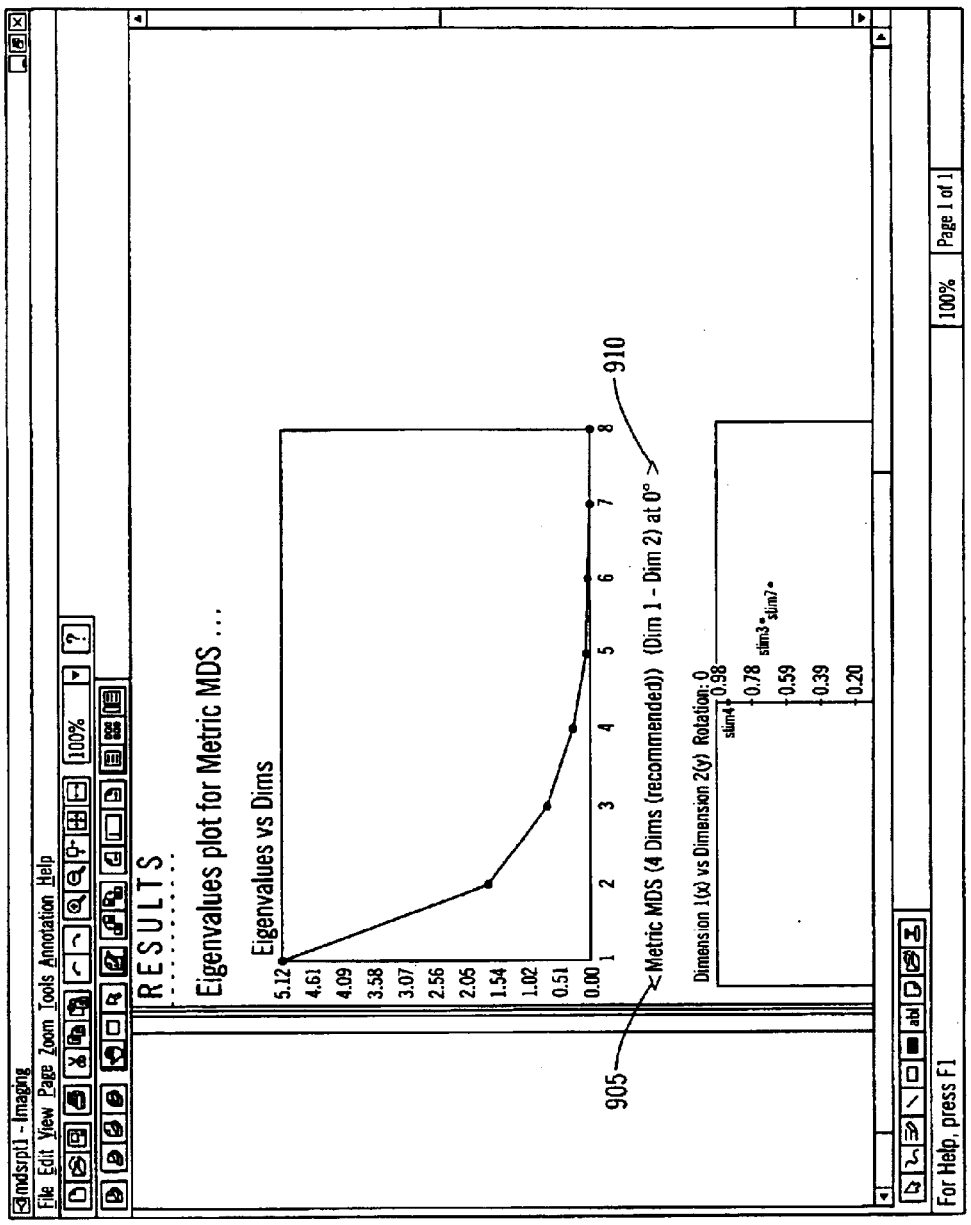
Figure 15:
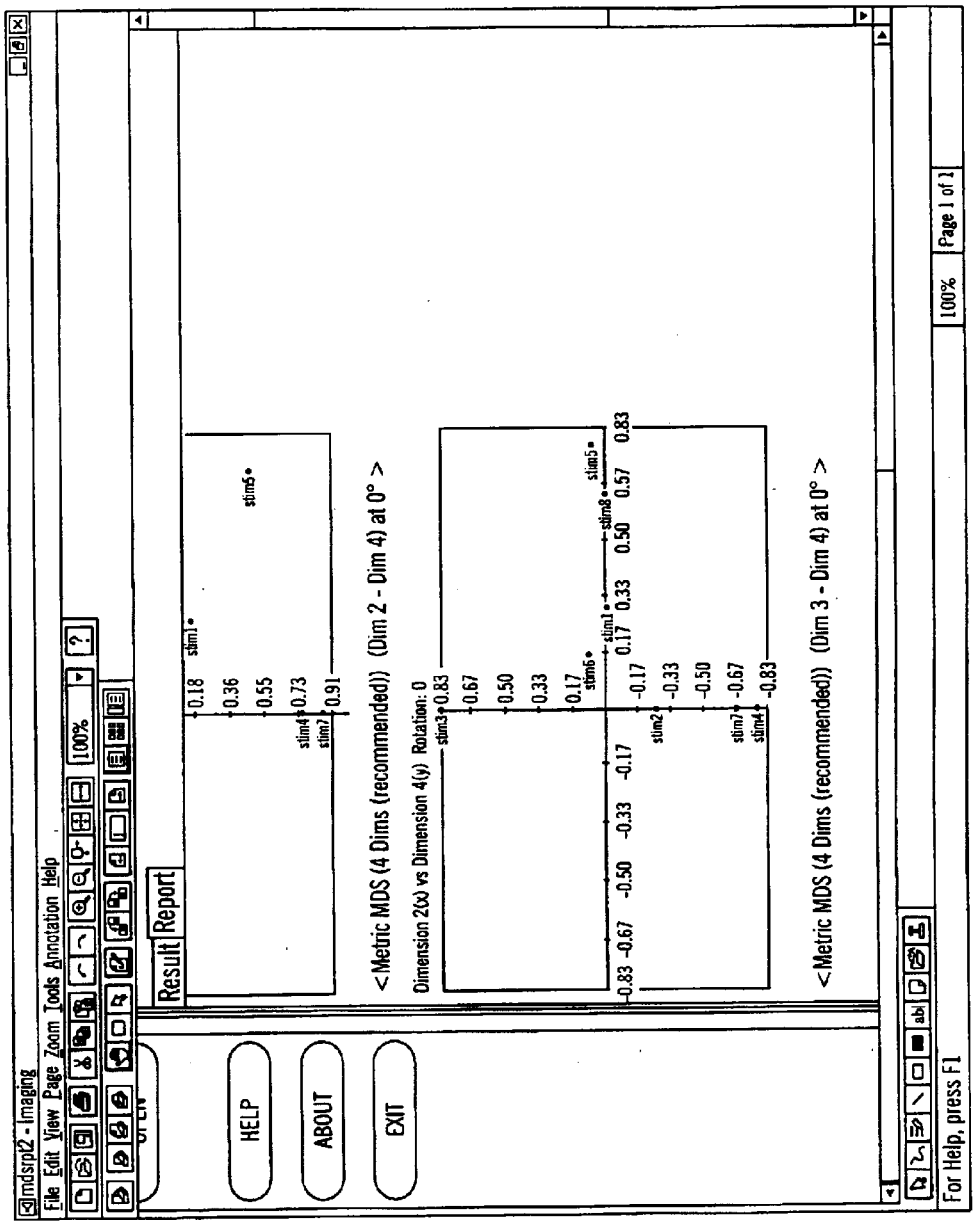
Figure 16:
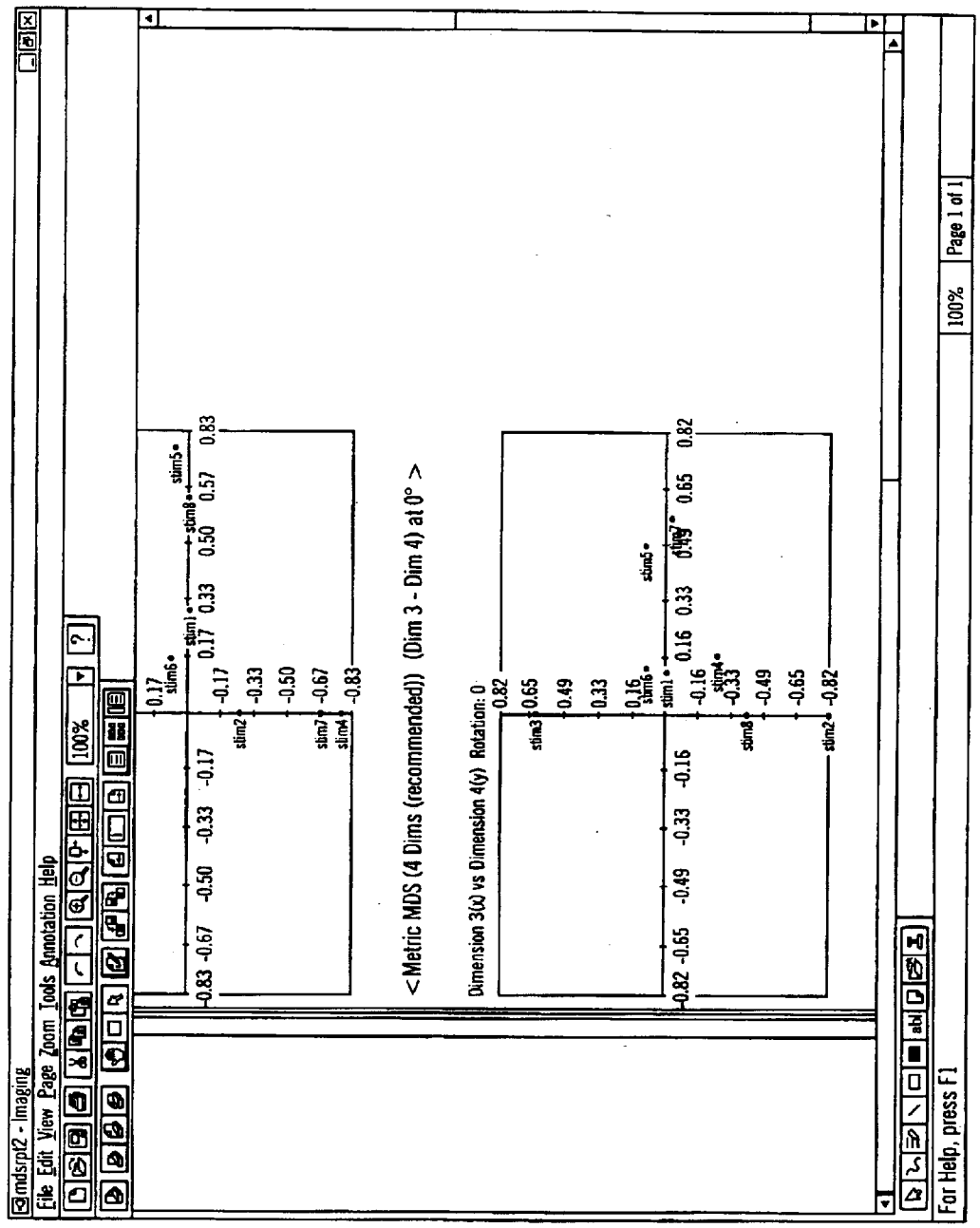

Once the plot is generated by the GUI program, spatial relationship between the factors can be evaluated by the experimenter for the test results plot. Multidimensional scaling analysis is used to determine which factors, such as half-tone screen, sharpening, smoothing, resolutions, etc., contribute to differences in print quality. As seen in FIG. 10, an initial comparison of the Stress (Non-Metric or "Eigenvalues" in Metric) vs. the number of factors ("Dims") is conducted to determine how many factors should be compared for optimal results. The GUI program is able to determine which statistical calculation (i.e. classical MDS or modern MDS) gives the better result and recommends the optimal number of factors to be compared. However, the GUI program is flexible enough to allow the experimenter to chose either the alternative statistical calculation or to change the number of factors to compare. A closeup example of the Stress vs. # of Dims graph of FIG. 9 is shown in FIG. 11, which shows that three factors (or Dims) gives the elbow point of the stress (or best interaction quotient). Thus, the elbow point represents the number of factors that should be compared in the report. The number of factors giving the elbow point of the stress is unique to each experiment. In addition, test result page (FIG. 9 and 10) also gives a plot showing the test results of the multidimensional scaling method. Each plot compares two factors at a time. FIG. 12 provides a closeup view of the test result plot comparing factor one (Dim 1) and factor two (Dim 2), where stimuli points refer to the results of different printers used. Similarly, the GUI program is also able to compare factors 2 vs. 3, and factors 1 vs. 3, by providing a drop down menu for the experimenter to select the factors to be compared. Each comparison will produce a unique plot. By looking at the spatial relationship between the plot points, a finding can be made based on the experimental data.

Once the desired plots are generated, the GUI program can automatically generate a test report at block 804 (FIG. 8). An example of the test report is shown in FIGS. 13-16. Information such as experiment name, purpose, experiment setup, number of images, the name of the factors, etc. as well as the test plots can be automatically be generated by the GUI program based on the information previously entered by the experimenter. In addition, preset paragraph descriptions can also be added by the GUI program to describe the results of the experiment depending on the actual results of the tests.

For MDS plot analysis, the plot can be better analyzed by rotating the plot such that specific points are aligned or the points are located opposite one another on a horizontal line. However, rotational analysis involves complex and tedious calculations to preserve the numerical value of the spatial relationships once the plot is rotated. In other words, each point on the plot (i.e. point corresponding to the text data) will have to be recalculated each time the plot is rotated. At block 805, the GUI program allows the experimenter to rotate the plot to the desired position and automatically recalculates the text data values as the plot is rotated. In preferred embodiments, the plot can be rotated by selecting the "<" icon 905 for counter clockwise rotation or the ">" icon 910 for clockwise rotation. The report will be automatically changed according to the change of the rotation angle or any other changes in the test result window. Once the desired position is reached, the experimenter can stop rotating the plot and use the new values (i.e. the automatically adjusted changes) for reporting the experimental results. For example, in comparing any two factors, the experimenter will have in mind what relationship he/she is looking for in the plot (e.g. the print algorithm represented by green and the print algorithm represented by red is opposite on a horizontal line). Similarly, the experimenter can rotate the other plots representing the other factor comparisons. At block 806, the experimenter can terminate the data analysis and the GUI program can print (i.e. a hardcopy) or save as a computer file (i.e. a softcopy) a final report including all of the rotated plots. In preferred embodiments, the softcopy is saved in text format which can be opened/edited by any known word processor. In alternative embodiments where more than one psychophysics test conducted, the experimenter may decide to include other test results in the same test report. If so, the GUI program would wait for the experimenter to select another test or test method. The process would be then be repeated for each additional test method with a different test results screen. If no more tests exist, the Data Analysis Program is completed.

Conclusions and Alternative Embodiments

This concludes the description of the preferred embodiments of the invention. The following describes some alternative embodiments for accomplishing the present invention.

The described implementation of the configuration discovery tool 100 may be implemented as a method, apparatus or article of manufacture using standard programming and/or engineering techniques to produce software, firmware, hardware, or any combination thereof. The term "article of manufacture" as used herein refers to code or logic implemented in hardware logic (e.g., an integrated circuit chip, Field Programmable Gate Array (FPGA), Application Specific Integrated Circuit (ASIC), etc.) or a computer readable medium (e.g., magnetic storage medium (e.g., hard disk drives, floppy disks, tape, etc.), optical storage (CD-ROMs, optical disks, etc.), volatile and non-volatile memory devices (e.g., EEPROMs, ROMs, PROMs, RAMs, DRAMs, SRAMs, firmware, programmable logic, etc.). Code in the computer readable medium is accessed and executed by a processor. The code in which preferred embodiments of the configuration discovery tool are implemented may further be accessible through a transmission media or from a file server over a network. In such cases, the article of manufacture in which the code is implemented may comprise a transmission media, such as a network transmission line, wireless transmission media, signals propagating through space, radio waves, infrared signals, etc. Of course, those skilled in the art will recognize that many modifications may be made to this configuration without departing from the scope of the present invention, and that the article of manufacture may comprise any information bearing medium known in the art.

Preferred embodiments described different experimenter and observer stations. In alternative embodiments, the experimenter station may be later used as an observer station.

The observer stations were described as personal computers. In further embodiments, the observer stations may comprise a basic input means and display device, without using a separate, stand-alone computer. In such case, entered data may be transmitted directly to the experimenter's station. Alternatively, the test may be administered remotely, where the observer stations are at remote locations.

In preferred embodiments, the subjects of the experiment were described as printer output printed according to different printing algorithms. However, the preferred embodiments for defining and administering a psychophysics experiment may apply to samples in any type of media, including text, images, sounds, motion pictures, etc. The observable samples that are the subject of the tests are not limited to print samples. In the event that samples in other types of media are used, the algorithms would be designed to generate output in that media type and would be the subject of the comparison.

In summary, preferred embodiments provide a method, system, and program for method, system, and program for defining and administering a test to determine human perceptions of observable samples. A displayable test building window includes input fields to receive input on at least one observable sample according to at least one type of experiment. Generated in a data gathering window is at least one perception input field for each observable sample and at least one type of experiment. The observer is capable of entering perception information in each input field concerning the observable samples. Observer perception input on the observable samples is received and stored. Statistical analysis is then performed on the entered perception input.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A program for comparing multiple factors using multidimensional scaling analysis, the program comprising computer usable media including at least one computer program embedded therein that causes the computer to perform:

generating at least one set of samples, where each sample in the set is created by a print algorithm combining a number of factors;

for each set, collecting data on observable relative differences between samples in the set;

performing multidimensional statistical analysis on the collected data; and displaying results of the statistical analysis as plots.

2. The program of claim 1 that causes the computer to further perform:

displaying a test building window including input fields to receive input on the at least one set of samples;

generating a data gathering window including at least one perception input field for each observable set, wherein an observer is capable of entering perception information in each input field concerning the observable set;

receiving observer perception input on the observable set; and storing the observer entered perception input.

3. The program of claim 2, wherein the observable sample is embodied in a medium that is a member of the set of mediums comprising: images, text, sound, and motion pictures.

4. The program of claim 1 that causes the computer to further perform:

interpreting the plots to determine human perceptions to variations of factors.

5. The program of claim 1 that causes the computer to further perform:

determining an optimal number of factors to be compared for interpretation of the collected data; and generating plots comparing two factors at a time.

6. The program of claim 1 that causes the computer to further perform: performing rotational analysis on the plots and generating a report based on the collected data.

7. The program of claim 1, wherein the algorithm comprises a printing algorithm to control a printer to print the observable sample on paper.

8. The program of claim 7, wherein the factors in the printing algorithm are a member of a set of factors comprising half-tone screen, sharpening, smoothing, and resolutions.

* * * * *